United States Patent [19]

Benko et al.

[11] Patent Number: 4,604,086
[45] Date of Patent: Aug. 5, 1986

[54] MULTIFUNCTION CENTRIFUGE

[75] Inventors: Éva Benko, Budapest; István Csabankó, Esztergom; Anikó Porkoláb; Zsolt Szabó, both of Budapest; Gábor Takács, Pomáz, all of Hungary

[73] Assignee: "Labor" Muszeripari Muvek, Hungary

[21] Appl. No.: 693,732

[22] Filed: Jan. 23, 1985

[30] Foreign Application Priority Data

Jan. 26, 1984 [HU] Hungary ................................ 319/84

[51] Int. Cl.⁴ .............................................. B04B 5/02
[52] U.S. Cl. ......................................... 494/16; 494/10
[58] Field of Search ...................... 494/16, 17, 18, 21, 494/10; 435/296; 436/45, 46; 422/100, 101, 102, 99, 104; 210/360.1

[56] References Cited

U.S. PATENT DOCUMENTS

| 3,982,162 | 9/1976 | Olliffe | 494/10 |
| 4,148,607 | 4/1979 | Bernoco | 494/10 |
| 4,343,709 | 8/1982 | Okumura | 494/10 |
| 4,456,581 | 6/1984 | Edelmann | 494/10 |

Primary Examiner—Robert W. Jenkins
Attorney, Agent, or Firm—Handal & Morofsky

[57] ABSTRACT

A multifunction centrifuge consists of a rotor 1 to which a plurality of centrifuge bowls 2 are rigidly fixed. Each bowl 2 has two chambers 3a, 3b connected with each other for free flow communication from either chamber to the other. One chamber 3a lies above the other 3b and is of a sack shape with a radially outwardly projecting closed bottom so that on stoppage of rotor rotation liquid therein flows back into the more deeply-lying other chamber 3b. The bowl 2 is light-transparent for photometric measurements.

2 Claims, 3 Drawing Figures

MULTIFUNCTION CENTRIFUGE

FIELD AND BACKGROUND OF THE INVENTION

This invention concerns a multifunction centrifuge which has a rotor rotatable about a vertical axis and at least two centrifuge chambers accommodated in the rotor.

Centrifuges are generally used for performing the operations of centrifugation, decanting or pouring off the floated-up fraction, mixing, suspending, photometry and the evaluation of the particle size distribution. However, known centrifuges can only perform some or the other, but not all of the tasks enumerated above. There is no known centrifuge which can perform all of these tasks. Some of the known multifunction centrifuges can be used for suspending and decanting but to use these for photometric measurement is very difficult because they employ outswinging centrifuge tubes for centrifuging. The so-called Coombs centrifuges, the Merz+Dabe and the Serval centrifuges are of this type.

Another type of automatic centrifuge is capable of suspending but has the disadvantage that the lighter fraction (buoyant material) is not separated from the sediment with sufficient distinctions. Moreover, photometric measurement during rotation, i.e. particle size analysis, is not possible.

A further disadvantage is that the process of mixing requires an intricate mechanical construction. This type of centrifuge cannot be manufactured in a small-size variant.

SUMMARY OF THE INVENTION

An aim of the invention is the elimination, or at least a substantial reduction, of the above-mentioned drawbacks and the provision of a multifunction centrifuge which has a simple mechanical construction and which, despite requiring little space, is suitable for the automatic performance of the above-listed functions.

The invention is based on the discovery that the above aim may be satisfied when the centrifuge 'bowls' serving as reaction chambers are so formed and rigidly fixed to the rotor in such a manner than upon stopping the rotor the lighter fraction of upfloating material, under the effect of gravity, flows off the sediment. When restarting the centrifuge, the lighter fraction under the effect of the centripetal force flows back onto the sediment.

Accordingly, the invention concerns a multifunction centrifuge having a rotor rotatable about a vertical axis and at least two centrifuge 'bowls' paced in the rotor. The improvement consists of the centrifuge 'bowls' being rigidly fixed to the rotor by the bracket-like retaining walls thereof and each centrifuge 'bowl' has an outer, sack-like or cylindrical centrifuge chamber having a constant cross-section with an outwardly facing bottom and an inner, more deeply lying gravitational chamber which is connected to the outer chamber so as to assure two-way free flow communication between the two chambers.

The rigid fixing of the centrifuge bowls makes it possible for them to rotate into the light path of the photometric measuring instrument, whereby it will enable photometry and particle size analysis to be performed. To assure that the lighter fraction, which in the stationary position of the rotor has separated from the sediment, can be sucked away, there is an opening above the deepest point of the gravitational chamber.

BRIEF DESCRIPTION OF THE DRAWING

Preferred embodiments of the invention are described purely by way of example in the accompanying schematic drawing, wherein.

DESCRIPTION OF THE PREFERRED EMBODIMENT

Figure 1:
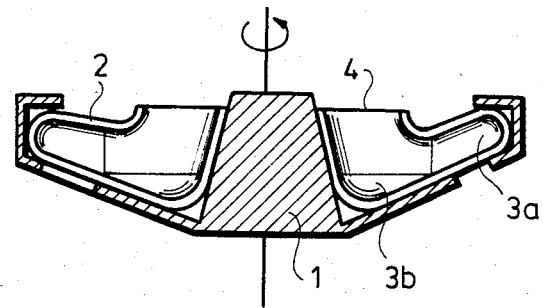
FIG. 1 is a cross-section of a centrifuge according to the invention.

In the embodiment of the centrifuge according to the invention illustrated in FIG. 1, a rotor 1 rotatable about a vertical axis has centrifuge bowls 2 rigidly fixed to the rotor. The centrifuge bowls each consists of two chambers 3a and 3b so connected with each other as to assure free throughflow in either direction. The outer chamber is a so-called centrifuge chamber 3a shaped somewhat like a sack and having an outwardly disposed bottom, while the inner chamber is a so-called gravitational chamber 3b, with a bottom lying more deeply than the chamber 3a.

Above the lowest-lying portion of the gravitational chamber 3b an opening 4 is provided for the charging and discharging of various materials. The rotor 1 is so formed that the centrifugal chamber 3a is light-transparent, i.e. can for example be rotated in the path of a light beam of a photometric instrument.

Figure 2:
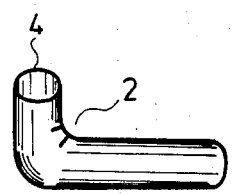
FIGS. 2 and 3 are perspective views of two different embodiments of the centrifuge bowl or chamber.

FIG. 2 illustrates a preferred embodiment of a centrifuge bowl which is formed from a tube bent at right-angles into an L shape.

Figure 3:
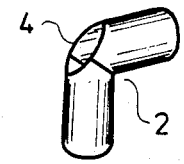

FIG. 3 shows a further embodiment of a centrifuge bowl consisting of two test tube pieces connected to each other at an angle greater than 90°.

In both embodiments, the opening 4 is above the deepest lying part of the centrifuge bowl.

In use of the multifunction centrifuge according to the invention, the suspension or slurry is accommodated in the centrifuge chamber 3a lying above the chamber 3b. On stopping the rotor, the suspension flows back freely into the gravitational chamber 3b. The periodic starting and braking of the rotor causes the liquid repeatedly to be displaced along the length of the centrifugal bowl which in turn means very effective mixing and suspending.

By passing a light beam through the centrifuge bowl 3a it is possible during rotation to monitor the optical density for a given level of the centrifuge bowls, that is to say, it is possible to follow its change with time or as a function of the centrifugal acceleration.

We claim:

1. A multifunction centrifuge comprising a rotor rotatable about a vertical axis and at least two centrifuge bowls disposed about the rotor, the improvement consisting in that the centrifuge bowls are rigidly connected to the rotor by bracket-like retaining walls thereof and each centrifuge bowl has an outer centrifugation chamber of sack-like or cylindrical shape having a constant cross-section with an outwardly facing bottom and an inner gravitational chamber connected to said outer chamber for bidirectional free communication, said gravitational chamber lying lower than the said outer chamber.

2. A multifunction centrifuge according to claim 1, wherein an opening is provided in the centrifuge bowl above the lowest lying part of the gravitational chamber.

* * * * *